United States Patent [19]

Samsel et al.

[11] Patent Number: 5,276,220

[45] Date of Patent: * Jan. 4, 1994

[54] ACTINIDE CATALYZED CHAIN GROWTH PROCESS

[75] Inventors: Edward G. Samsel; David C. Eisenberg, both of Baton Rouge, La.

[73] Assignee: Ethyl Corporation, Richmond, Va.

[*] Notice: The portion of the term of this patent subsequent to May 11, 2010 has been disclaimed.

[21] Appl. No.: 900,387

[22] Filed: Jun. 18, 1992

[51] Int. Cl.$^5$ ............... C07C 29/54; C07C 31/125; C07C 2/88; C07F 5/06

[52] U.S. Cl. .................. 568/911; 556/190; 585/637

[58] Field of Search ............. 568/911; 556/190; 585/637

[56] References Cited

U.S. PATENT DOCUMENTS

| | | | |
|---|---|---|---|
| 3,030,398 | 4/1962 | Shapiro et al. | 556/190 |
| 3,322,806 | 5/1967 | Asinger et al. | 568/911 |
| 3,328,447 | 6/1967 | Kottenhahn | 556/190 |
| 3,347,894 | 10/1967 | Trebillon et al. | 568/911 |
| 3,382,269 | 5/1968 | Williams et al. | 556/190 |
| 4,665,046 | 5/1987 | Campbell | 502/102 |

FOREIGN PATENT DOCUMENTS 768083 2/1957 United Kingdom ............... 556/190

OTHER PUBLICATIONS

Websters Third New International Dictionary, unabridged, pp. 24–28, 1961.

*Primary Examiner*—Joseph E. Evans
*Attorney, Agent, or Firm*—David M. Bunnell

[57] ABSTRACT

An improved process for preparing an alkyl chain growth product by the chain growth reaction of α-olefin in an aluminum alkyl uses a catalyst system which comprises an actinide metallocene.

30 Claims, No Drawings

ACTINIDE CATALYZED CHAIN GROWTH PROCESS

This invention relates generally to the preparation of aluminum alkyls by the chain growth reaction of a lower olefin, especially ethylene, with a lower molecular weight alkyl aluminum and more specifically to an improved chain growth process catalyzed by derivatives of actinide series metallocenes in combination with aluminoxanes or, alternatively, cationic actinide metallocene complexes containing inert, non-coordinating anions, either alone or in combination with aluminoxanes.

Stepwise ethylene chain growth on aluminum alkyls was discovered in the 1950's by K. Ziegler et al. The reaction, shown in equation 1 (where R—Al represents a single chain on the trialkylaluminum), proceeds thermally at temperatures in the range of 100°-200° C. under high ethylene pressure, typically 2000-4000 psi. At higher temperatures, the displacement reaction shown in equation 2 competes with chain growth, producing $\alpha$-olefins and ethyl aluminum alkyls. For a review see "Comprehensive Organometallic Chemistry:, 1982, Pergammon Press, Vol. 7, Section 46.

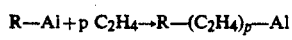

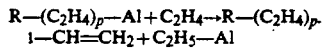

The manufacture of $\alpha$-olefins using these reactions is commercially practiced. An Ethyl Corporation process gives olefin chain lengths of $C_4$ to $C_{22+}$ which are essentially described by the Poisson distribution, modified by some olefin recycle operations. The Poisson statistical distribution is described below. The typical linear $\alpha$-olefin content (purity) at various carbon numbers is shown in the following chart; the other components are branched $\alpha$-olefins (vinylidenes), linear internal olefins and small (<1%) amounts of paraffin.

|  | $C_6$ | $C_8$ | $C_{10}$ | $C_{12}$ | $C_{12-14}$ | $C_{14-16}$ |
|---|---|---|---|---|---|---|
| wt. % $\alpha$-olefin | 97.5 | 96.5 | 96.2 | 93.5 | 87.0 | 76.9 |

Aluminum alkyl chain growth catalyzed by transition metal compounds is described in commonly owned co-pending application Ser. No. 07/881,928, filed May 12, 1992, now U.S. Pat. No. 5,210,338, which is a continuation-in-part of abandoned application Ser. No. 782,116, filed Oct. 25, 1991. According to this process, metallocene halo complexes of zirconium and hafnium and related catalysts in combination with methylaluminoxane (MAO), produce aluminum alkyls where the ethylene chain growth products are best described by the Schulz-Flory statistical distribution; polyethylene is a persistent co-product. The Schulz-Flory distribution is described by the formula $\chi_p = \beta/(1+\beta)^p$, where $\chi_p$ is the mole fraction containing p added ethylenes and $\beta$ is the Schulz-Flory distribution coefficient. The process of the present invention also operates at mild temperatures and pressures to produce purer $\alpha$-olefin products but is dissimilar to the process of Ser. No. 07/881,928 in that it can provide a Poisson type chain length distribution and avoid polyethylene co-product.

In accordance with this invention there is provided an improved process for the preparation of an aluminum alkyl chain growth product by the chain growth reaction of $\alpha$-olefin on an aluminum alkyl, the improvement comprising catalyzing the chain growth reaction with a catalyst system which comprises an activated actinide metallocene.

Also provided is an improved process for the preparation of linear alpha-olefins by the chain growth reaction of $\alpha$-olefin on an aluminum alkyl followed by olefin displacement of linear alpha-olefins from the aluminum alkyl chain growth product, the improvement comprising catalyzing the chain growth reaction with a catalyst system which comprises an activated actinide metallocene.

Also provided is an improved process for the preparation of linear primary alcohols by the chain growth reaction of $\alpha$-olefin on an aluminum alkyl followed by oxidation of the aluminum alkyl chain growth product to form alkoxides and acid hydrolysis of the alkoxides to produce linear primary alcohols, the improvement comprising catalyzing the chain growth reaction with a catalyst system which comprises an activated actinide metallocene.

Examples of $\alpha$-olefins suitable for chain growth include, but are not limited to, $C_2$ to $C_6$ straight chain $\alpha$-olefins, with ethylene being the preferred olefin.

This invention provides a process for chain growth on aluminum alkyls which occurs at mild temperatures and pressures and is capable of giving very pure oligomer chains. It utilizes a highly active catalyst which comprises an actinide metallocene derivative with, in some formulations, a hydrocarbyl aluminoxane co-catalyst. The process gives oligomer chain lengths described by the Poisson distribution as described below. In practice, $\alpha$-olefins can be recovered from the product aluminum alkyls by thermal displacement (eq. 2) or by catalyzed displacement with ethylene or 1-butene. Ziegler-Natta catalysts of the type useful in the process of the invention were discovered by Kaminsky et al. (Angew. Chem. Int. Ed. Engl., 1976, Vol. 15, pages 630-632), and enjoy widespread interest as olefin polymerization catalysts. The active catalysts are thought to be cationic, coordinatively unsaturated transition metal alkyl complexes which rapidly insert olefins to grow polymer chains. Chain growth is terminated principally by $\beta$-hydrogen or $\beta$-alkyl elimination to give a vinylic end group or by hydrogenolysis to give a paraffinic end group; these reactions generate a catalytically active metal hydride or alkyl.

In this invention, the same or similar catalytic species probably operate but chain growth is terminated by the efficient transfer of the chain to aluminum alkyl, which is present as solvent or co-solvent. This alkyl group interchange, depicted in eq. 3 (where M is the catalyst metal center), generates a new catalytically active actinide metal alkyl complex.

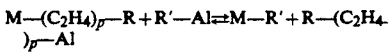

According to the invention, growth of alkyl chains on aluminum alkyls, as shown in equation 4, is catalyzed by derivatives of actinide series metallocenes in combination with aluminoxanes; alternatively, cationic actinide metallocene complexes with a hydrocarbyl ligand or hydride containing inert, non-coordinating anions may be used alone or in combination with aluminoxanes. In the equation, R represents H or a $C_2$ to $C_{40}$ alkyl chain; these alkyl groups may be mixed on Al or a homoleptic trialkyl aluminum may be used. The length of the product alkyl chains essentially follow the Poisson statistical distribution, at least at low pressures. This statistical distribution is described by: $\chi_p = (x^p e^{-x})/p!$, where $\chi_p$ is the mole fraction with p added ethylenes and x is the Poisson distribution coefficient equal to the average number of ethylenes added per Al—C bond. The product distribution obtained with the actinide catalysts can also be altered, by proper choice of reaction conditions, so that the chain length is best described by a Schulz-Flory distribution. Other reaction conditions can be found in which the product distribution does not fit either statistical function, but has similarities to both. The Schulz-Flory distribution may be desirable in some situations, for example chain growth on TNBA to give primarily $C_6$ followed by displacement by 1-butene to regenerate TNBA. This modification is most readily accomplished at higher ethylene pressures and lower temperatures. With the actinide based catalysts, polyethylene is seldom a co-product.

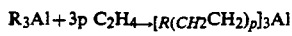

4.

The present invention differs from the process of application Ser. No. 07/881,928, which utilizes transition metal catalysts, in two respects. First, the Poisson distribution peaks at discrete chain lengths, governed by the choice of starting aluminum alkyl and the value of x. Thus when triethylaluminum (TEA) is the starting substrate, the valuable $C_6$ and $C_8$ fractions can be made to predominate, minimizing the production of the less desirable $C_4$ and $C_{10+}$ fractions. With the Schulz-Flory distribution, the shortest grown chain (p=1) always predominates, so that TEA produces primarily $C_4$. The second difference is that no polyethylene co-product is formed. This co-product is always present when using the transition metal catalysts and such polyethylene is undesirable because it not only reduces the yield but it complicates the processing of the product.

Suitable activated actinide metallocene catalyst systems for use in the process of the invention include:

(A) an uncharged actinide metallocene derivative and a hydrocarbylaluminoxane, (B) a cationic actinide metallocene complex with a hydrocarbyl or hydride ligand containing an inert, non-coordinating anion, and (C) a cationic actinide metallocene complex with a hydrocarbyl ligand or hydride containing an inert non-coordinating anion, and a hydrocarbylaluminoxane.

The primary catalyst is an organometallic compound of an actinide series element (elements having atomic numbers of 90 to 103), and preferably, thorium or uranium; the metal may be in a formal oxidation state of +4 or +3. As used herein, the term "metallocene" includes actinide metal derivatives which contain at least one cyclopentadienyl moiety. The catalyst structures may be described as metallocene (or bent metallocene in the case of bis-cyclopentadienyl derivatives) with ancillary anionic ligands or hydrocarbyl groups, such as $Z_t$ $(\eta^5-R'_nH_mC_5)_sMX_{r-s}$, where R' is a carbon or carbon and heteroatom (N, O, S, P, B, Si and the like) containing group such as $C_1$ to $C_{20}$ alkyl, $C_3$ to $C_{12}$ cycloalkyl, $C_7$ to $C_{20}$ aralkyl or $C_6$ to $C_{14}$ aryl. Non-limiting examples of such R' groups include methyl, ethyl, trimethylsilyl, t-butyl, cyclohexyl, phenyl, 4-methylphenyl, 2,4,6-trimethylphenyl, 2-phenylethyl and the like. The R' substituents can be different in type and in number on each cyclopentadienyl ring and can form fused cyclic groups attached to the rings. Z is a bridging group between rings such as silane, phosphine, amine or carbon groups, t is 0 or 1, m and n are integers of 0 to 5, m+n=5 (or 4 if Z is present), r is 3 or 4, s is 1 or 2 when r=3 and 1 to 3 when r=4, M is a actinide element and especially Th or U, X is halogen, psuedohalogen (e.g. a leaving group in nucleophilic substitution such as ester, alkoxide, cyanide, tosylate, triflate, $\beta$-diketonate and the like), hydride or $C_1$ to $C_8$ alkyl or aryl. Analogous metallocenes with two different X groups are also useful. Useful complexes where the metal is in the +3 formal oxidation state, are described by the formula $Z_t$ $(\eta^5-R'_nH_MC_5)_2MX$. Useful complexes also include compounds of the type $(\eta^5-R'_nH_mC_5)MX_3$, and $(\eta^5-R'_nH_mC_5)_3MX$. Also potentially useful are oxygen bridged dimers such as $[(\eta^5-R'_mH_nC_5)_2MX]_2(\mu-O)$ where R', M, X, n and m are as defined above.

Specific non-limiting examples of such metallocenes include bis(1,3-di(trimethylsilyl)cyclopentadienyl)thorium dichloride,
bis(1,3-di(trimethylsilyl)cyclopentadienyl)uranium chloride,
bis(1,3-di(trimethylsilyl)cyclopentadienyl)uranium dichloride,
bis(pentamethylcyclopentadienyl)thorium dichloride,
bis(pentamethylcyclopentadienyl)uranium dichloride,
bis(pentamethylcyclopentadienyl)uranium chloride trimer,
bis(pentamethylcyclopentadienyl)uranium chloride sodium chloride adduct,
bis(pentamethylcyclopentadienyl)uranium chloride potassium chloride adduct,
bis(trimethylindenyl)thorium dichloride,
bis(trimethylindenyl)uranium dichloride,
bis(ethyltetramethylcyclopentadienyl)thorium dichloride,
bis(ethyltetramethylcyclopentadienyl)uranium dichloride,
dimethylsilanyl bridged bis(tetramethylcyclopentadienyl)thorium dichloride,
dimethylsilanyl bridged bis(tetramethylcyclopentadienyl)uranium dichloride,
dimethylsilanyl bridged bis(tetramethylcyclopentadienyl)thorium dihydride dimer,
dimethylsilanyl bridged bis(tetramethylcyclopentadienyl)thorium dimethyl,
methylene bridged bis(cyclopentadienyl)thorium dichloride,
methylene bridged bis(cyclopentadienyl)uranium dichloride,
dimethylsilanyl bridged bis(cyclopentadienyl)thorium dichloride,
dimethylsilanylbridged bis(cyclopentadienyl)uranium dichloride,
meso and racemic dimethylsilanyl bridged bis(indenyl)thorium dichloride,
meso and racemic dimethylsilanyl bridged bis(indenyl)uranium dichloride,
and the like.

Another useful form of the primary catalyst is a cationic metallocene alkyl (or aryl or hydride) salt containing an inert, essentially non-coordinating anion. This form may be used alone or in conjunction with the hydrocarbyl aluminoxane additives which increase the catalysts' activity and lifetimes. The cationic catalysts may be used as isolated solids or as catalyst liquors generated by the admixture of appropriate precursors, described below, without isolation of the catalyst salts.

Several classes of precursors are appropriate. The metallocene dialkyls (or diaryls or mixed aryl alkyls) described above may be treated with salts wherein the cation is a Bronsted-Lowry acid which is able to remove one alkyl group from the metal to generate alkane, the metal cation with inert anion, and a neutral, poorly coordinating base (e.g. tributylamine or N,N-dimethylaniline). Such precursors are known in the art and are extensively described, for example, in International Application No. PCT/US91/04390, Publication No. WO 92/00333, published Jan. 9, 1992, whose teachings are incorporated herein by reference. A non-limiting example is given in equation 5 for clarification, where the anion A is described below, where Cp* represents $\eta^5-C_5(CH_3)_5$, Me is $CH_3$ and Ph is $C_6H_5$.

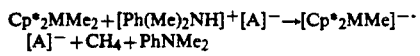

$$Cp^*{}_2MMe_2 + [Ph(Me)_2NH]^+[A]^- \rightarrow [Cp^*{}_2MMe]^{-\cdot}[A]^- + CH_4 + PhNMe_2 \qquad 5.$$

A second general class of precursors are metallocene dialkyls and salts, wherein the cation is an oxidizing agent, such as ferrocenium, triphenylcarbenium, silver ion and the like. In this case, the oxidizer presumably serves to generate a transient metallocene dialkyl radical cation which decays by loss of a alkyl radical to generate the catalyst cation salt. A non-limiting example is given for clarification in equation 6, where Fc represents ferrocene, $(\eta^5-C_5H_5)_2Fe$.

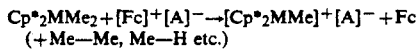

$$Cp^*{}_2MMe_2 + [Fc]^+[A]^- \rightarrow [Cp^*{}_2MMe]^+[A]^- + Fc$$
$$(+Me-Me, Me-H \text{ etc.}) \qquad 6.$$

The required qualities of the anion A are that it be inert toward reaction with the cationic catalyst, non-coordinating, bulky and unreactive toward the aluminum alkyl medium. Typical examples of A are $B(C_6F_5)_4$, $B[3,5-(CF_3)_2C_6H_4]_4$, $B(4-FC_6H_4)_4$; closo-carborane anions such as $CB_{11}H_{12}$ function as A as do closo-borane dianions such as $B_{10}H_{10}$ (forming salts of the type $M_2A$). Other anions can also be used as would be readily apparent to those skilled in the art in view of the above examples.

A third general method of generating the catalytically active cations is the abstraction of an alkyl group from the metallocene dialkyl by a powerful Lewis acid to produce the mono-alkyl cation and a anionic conjugate base which is inert to the medium and poorly coordinating. The catalyst liquor may be prepared without isolation of the salt (or Lewis acid/base adduct) which probably exists in solution as a dynamic equilibrium. A non-limiting example is shown in equation 7 for illustration.

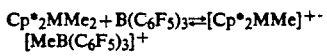

$$Cp^*{}_2MMe_2 + B(C_6F_5)_3 \rightleftharpoons [Cp^*{}_2MMe]^{+\cdot}[MeB(C_6F_5)_3]^+ \qquad 7.$$

Yet another useful type of catalyst is a neutral monoalkyl (or aryl or hydride) complex containing one cyclopentadienyl or substituted Cp ligand and one 6-electron donor dianionic ligand. Examples are the complexes $(\eta^5-C_5(CH_3)_5)$ $(\eta^5-C_2B_9H_{11})MCH_3$, where the boron ligand is a nido-dicarbolide dianion.

The hydrocarbyl aluminoxane co-catalysts are solutions or slurries in hydrocarbon solvent of oligomers of the general formula $(R''AlO)_y$ where $R''$ is $C_2$ to $C_{10}$ alkyl and y is 5 to about 40 formed by partial hydrolysis of aluminum alkyls or mixtures of aluminum alkyls, according to procedures known in the art. Particularly effective are methyl aluminoxane (MAO, $R''$=methyl) and "modified" MAO ($R''$=methyl+octyl) prepared by partial co-hydrolysis of trimethylaluminum (TMA) and a long chain aluminum alkyl such as tri-n-octylaluminum (TNOA). When cationic alkyl complexes are used as catalysts, other aluminoxanes such as isobutyl aluminoxane (IBAO), produced from triisobutylaluminum (TIBA), are useful in enhancing catalytic activity.

The chain growth reaction illustrated in equation 4 may utilize a neat aluminum alkyl medium or may utilize a hydrocarbon solvent diluent such as toluene or heptane. When the chain is being grown by ethylene, higher ($C_3-C_{20+}$ alpha-olefins such as 1-octene may be used as a solvent or co-solvent, albeit with some decrease in product purity. Reaction temperatures may vary from approximately room temperature (20° C.) to 150° C., with higher temperatures tending to increase olefinic and branched impurities. Pressures of ethylene may be varied from about 15 psig to about 1000 psig.

The mole ratio of catalyst to aluminum alkyl may be varied from about $1 \times 10^{-7}$ to $1 \times 10^{-1}$ and preferably from about $1 \times 10^{-6}$ to $1 \times 10^{-2}$, and more preferably is in the range $2 \times 10^{-6}$ to $5 \times 10^{-3}$.

With the neutral catalysts (e.g. metallocene dihalides), the mole ratio of aluminoxane to catalyst, expressed as moles of total aluminum in the aluminoxane, may range from about 5/1 at high catalyst concentrations to about 50,000/1 at low catalyst concentrations. With some of the catalysts, it is beneficial to add the aluminoxane in portions throughout the reaction, or to add it continuously by means of a pump. This prolongs catalyst lifetimes and increases the value of x. With the cationic monoalkyl catalysts, no aluminoxane co-catalyst is required although aluminoxane (e.g. MAO or IBAO) can be useful in extending the catalyst lifetimes, especially at higher temperatures.

When conducting the chain growth reaction with some catalysts, it is helpful to activate the catalyst in order to avoid an induction period. Two methods are convenient. In one method, the catalyst is heated (60° to 120° C., for example) in the aluminum alkyl under ethylene for 10–20 minutes prior to addition of the aluminoxane co-catalyst, whereupon immediate ethylene uptake occurs. In the second method, the catalyst is incubated in aluminoxane solution in a separate vessel for about 5 minutes at 20° C. Subsequent addition to the aluminum alkyl permits immediate uptake of ethylene.

The aluminum alkyl feed compounds for the chain growth include trialkyl aluminums and dialkyl aluminum hydrides which can be represented by the formula $R_mAlH_n$ where m is 2 or 3 and n is 0 or 1, m+n=3, and R is $C_2$ to $C_{20}$ alkyl which can be the same or different. Mixtures of these compounds can be used. Specific non-limiting examples of suitable feed compounds include triethylaluminum, tri-n-propylaluminum, tri-n-butylaluminum, tri-n-hexylaluminum, diethylaluminum hydride, and the like.

Preferred aluminum alkyl feed stocks for the chain growth process are low molecular weight aluminum alkyls having alkyl groups with even carbon numbers and especially triethylaluminum (TEA) and tri-n-butylaluminum (TNBA).

$C_4$ to $C_{20+}$ alpha-olefins can be recovered from the alkylaluminum chain growth products by thermal or catalytic displacement by known procedures such as, for example, using ethylene and/or butene as the displacing olefin as described in U.S. Pat. No. 4,935,569. Alternatively, the chain growth products can be oxidized and hydrolyzed using known procedures to produce linear primary alcohols.

The invention is further illustrated by, but is not intended to be limited to, the following general procedures and examples.

Manipulation of catalysts, aluminum alkyls, and aluminoxanes, as well as the assembly and disassembly of reactors were conducted in a nitrogen filled glovebox. The addition of aluminoxanes to the reactor was done by syringe under flow of nitrogen or ethylene, as described below. The aluminum alkyls triethylaluminum (TEA), tri-n-butylaluminum (TNBA) and tri-isobutylaluminum (TIBA) are commercial products of Ethyl Corporation as is methyl aluminoxane (MAO) which is provided as a solution in toluene. "Modified" MAO is a developmental product of Ethyl Corporation, which consists of the co-hydrolysis products of trimethyl-aluminum (TMA) and tri-n-octylaluminum (TNOA) (5:1 mole ratio) in toluene. Iso-butylaluminoxane (IBAO) was prepared by careful hydrolysis of a TIBA solution in toluene using 0.9 equivalents of water. Ethylene was polymer grade, used without purification. Other solvents and reagents were dried and degased by conventional methods. Preparation of the primary actinide catalyst compounds was conducted by conventional methods described in the literature (see, for example, Marks, T. J. et al *J. Am. Chem. Soc.* 1981, 103, 6650–6657).

Quantitative analysis of aluminum alkyl reaction products was conducted as follows. While assembling the reactor, a known amount of n-undecane was added to the reaction mixture. After reaction completion, a small aliquot of the product in toluene was hydrolyzed with O$_2$-free aqueous HCl (20%). Analysis of the product hydrocarbons by gas chromatograph utilized a Hewlett-Packard 5890-II instrument, a model 3396-II integrator and a 50 m, 0.2 mm i.d. capillary column bonded with HP-1 phase. The data, moles of n-alkane vs p, were reiteratively fitted to the appropriate distribution function to obtain best-fit values of the distribution coefficients.

Reactions were conducted in a 6-oz. Fischer-Porter pressure bottle connected with O-ring and stainless steel adapter to a pressure head. This head consists of a stainless steel cross-tee fitted with a steel ball valve directly above the bottle, fitted on one side-arm with a needle valve connected to ethylene and connected on the other side-arm to a steel tee fitted with a pressure gauge and with a pressure relief valve. This arrangement allows a syringe needle to deliver aluminoxane or other liquids directly into the reaction bottle.

Results of reactions conducted using this apparatus are given in Table 1. Details of Examples 1, 11, 13 and 20 are given here to exemplify the experimental procedures. The process variations with respect to catalysts, reactant, solvents, reaction conditions, etc. for the other examples are described in Table 1. The oligomer distributions and purities for Examples 1, 11, 13 and 20 are shown in Table 2.

EXAMPLE 1

Into the Fischer-Porter bottle was weighed 15 mg (0.026 mmol) of $\eta^5$—C$_5$(CH$_3$)$_5$)$_2$ThCl$_2$ and undecane (200 $\mu$L), TEA (5 mL, 36.5 mmol) and toluene (5 mL) were added. The apparatus was assembled, briefly evacuated through the ball valve, and then pressurized to 100 psig with ethylene and heated in an oil bath at 70° C. for 10 min. MAO in toluene (1.0 ml, octyl modified, 5.8 wt % Al) was added via syringe through the ball valve, and ethylene uptake commenced immediately. The reaction continued for 30 more min. with two 1.0 mL portions of MAO being added at 10 min. intervals. A small aliquot diluted in toluene was hydrolyzed and analyzed. The resulting data was fitted to the Poisson distribution to give $x = 2.57 \pm 0.02$.

EXAMPLES 2–10

Examples 2–10 were conducted in similar manner to the process described in Example 1. The reactants, proportions and reaction conditions are listed in Table 1.

EXAMPLE 11

A stock solution was prepared as follows. ($\eta^5$—C$_5$(CH$_3$)$_5$)$_2$UCl$_2$ (30 mg, 0.052 mmol) in 3 ml of toluene was treated with 163 $\mu$L of a sodium napthalinide solution (0.317M) in THF. This solution was filtered, the solvent was removed under vacuum and the green residue was dissolved with toluene and diluted to 5.0 mL to give the known compound ($\eta^5$—C$_5$(CH$_3$)$_5$)$_2$UCL$_2$ Na.n THF (0.010M, n=1–2); see Organometallics vol. 1, 1982, pages 170–180.

A Fischer-Porter bottle was loaded with TEA (5.0 mL, 36.5 mmol), 5 mL of toluene, undecane and 1.0 mL of the stock solution. The bottle was heated at 80° C. for 15 min. under 100 psig of ethylene, then MAO in toluene (0.50 mL, octyl modified, 5.8 wt % Al) was added via syringe and uptake commenced immediately. The reaction was allowed to continue for 20 min. at 80° C., with a second addition of MAO (0.50 mL) after 11 min. The apparatus was vented and an aliquot hydrolysed and analyzed to give data which was fitted to give a value of $x = 2.36 \pm 0.02$.

EXAMPLE 12

Example 11 was repeated except that neat TNOA was substituted for the TEA and toluene. The reaction parameters are listed in Table 1.

EXAMPLE 13

A stock solution consisting of $\eta^5$—C$_5$(CH$_3$)$_5$)$_2$Th(CH$_3$)$_2$ (52 mg, 0.098 mmol) and [Ph(CH$_3$)$_2$NH][B(C$_6$F$_5$)$_4$] (86 mg, 0.108 mmol) in 5.0 mL of toluene was prepared under N$_2$; this solution was stirred 10 min until gas evolution (CH$_4$) ceased and was stored at $-20°$ F. (N$_2$).

To a Fischer-Porter bottle was added TEA (5.0 mL), toluene (4.0 mL) and undecane (200 $\mu$L). The mixture was thermally equilibrated in a water bath at 21° C. under 100 psig of ethylene. A part of the stock solution (1.0 mL, 0.020 mmol Th) was added via syringe, resulting in immediate, sustained ethylene uptake; the bath temperature was maintained at 25°–33° C. After 23 min, pressure was released and an aliquot was hydrolyzed and analyzed, revealing a value of $x = 2.54 \pm 0.03$.

EXAMPLES 14–19

Examples 14–19 were conducted in a manner similar to the process of Example 13. The reaction parameters are given in Table 1. Examples 17–19 also included an aluminoxane cocatalyst.

EXAMPLE 20

A stock solution was prepared under $N_2$ from $(\eta^5-C_5(CH_3)_5)_2Th(CH_3)_2$ (28 mg, 0.053 mmol) and $B(C_6F_5)_3$ (26 mg, 0.051 mmol) in 5.0 mL of toluene.

To a Fischer-Porter bottle was added TEA (5.0 mL), toluene (5.00 mL), undecane, 1.0 mL of IBAO solution (3.9 wt. % Al) and part of the stock solution (0.50 mL, 0.0053 mmol Th). The vessel was equilibrated in a 95° C. bath, evacuated and pressurized to 100 psig of ethylene. After 20 min a further portion (1.0 mL) of IBAO solution was added via syringe. After 30 min. the pressure was vented, an aliquot in toluene was hydrolyzed and analyzed, revealing a value of $x = 2.25 \pm 0.05$.

EXAMPLES 21-24

Examples 21-25 were conducted in a manner similar to the previous Examples except that Example 21 did not include aluminoxane, and that Example 25 used 1-octene as a co-solvent. The reaction parameters are given in Table 1.

TABLE 1

Chain Growth by Actinide Catalysts

| Example | $R_3Al^1$ mmol | Catalyst$^2$ mmol | Aluminoxane$^3$ mmol | Temperature$^4$ °C. | Time Min | $x^5$ |
|---|---|---|---|---|---|---|
| 1 | TEA 36.5 | A 0.026 | MAO 5.6 (3 parts) | 80 | 30 | 2.6 |
| 2[6] | TEA 36.5 | A 0.023 | MAO 3.7 (2 parts) | 25 | 15 | 1.7 |
| 3[6] | TEA 36.5 | A 0.026 | MAO 2.8 | 70 | 10 | 1.1 |
| 4[6] | TEA 36.5 | A 0.021 | MAO 5.6 (3 parts) | 70 | 30 | 2.4 |
| 5 | TEA 36.5 | A 0.021 | MAO 0.94 | 55 | 34 | 2.0 |
| 6 | TEA 36.5 | A 0.019 | MAO 0.94 | 75 | 20 | 1.5 |
| 7[7] | TEA 36.5 | A 0.019 | MAO 0.94 | 85 | 15 | 1.2 |
| 8 | TEA 36.5 | A 0.014 | MAO 0.94 | 80 | 15 | 0.67 |
| 9 | TNBA 20.8 | A 0.014 | MAO 0.94 | 85 | 15 | 1.7 |
| 10 | TEA 36.5 | B 0.014 | MAO 0.94 | 85 | 15 | 1.7 |
| 11 | TEA 36.5 | C 0.010 | MAO 1.87 (2 parts) | 80 | 20 | 2.4 |
| 12[8] | TNOA 27.2 | C 0.015 | MAO 3.74 (2 parts) | 95 | 30 | 1.9 |
| 13 | TEA 36.5 | D 0.020 | none | 25 | 23 | 2.5 |
| 14 | TEA 36.5 | D 0.010 | none | 0 | 20 | $\beta = 0.74$ |
| 15 | TEA 36.5 | D 0.020 | none | 55 | 10 | 1.0 |
| 16 | TEA 36.5 | D 0.020 | none | 85 | 10 | 0.72 |
| 17 | TEA 36.5 | D 0.010 | IBAO 0.62 | 55 | 15 | 1.1 |
| 18 | TEA 36.5 | D 0.010 | IBAO 1.24 (2 parts) | 85 | 25 | 1.4 |
| 19 | TEA 36.5 | D 0.010 | IBAO 2.47 (4 parts) | 85 | 40 | 1.8 |
| 20 | TEA 36.5 | E 0.005 | IBAO 2.47 (2 parts) | 95 | 30 | 2.25 |
| 21 | TEA 36.5 | E 0.005 | none | 55 | 25 | 1.28 |
| 22 | TEA 36.5 | E 0.005 | MAO 1.87 | 80 | 35 | 2.0 |
| 23 | TEA 36.5 | F 0.019 | IBAO 3.72 (3 parts) | 85 | 30 | $\beta = 0.64$ |
| 24 | TEA 36.5 | G 0.19 | IBAO 3.72 (3 parts) | 85 | 30 | $\beta = 0.65$ |
| 25[9] | TEA 36.5 | C 0.009 | MAO 2.8 (3 parts) | 85 | 25 | 2.8 |

[1] Conducted in 50% (v/v) $R_3Al$/toluene at 100 psig unless otherwise noted.
[2] Catalysts used - A, $[\eta^5-C_5(CH_3)_5]_2ThCl_2$; B, $[\eta^5-C_5(CH_3)_5]_2UCl_2$; C, $[\eta^5-C_5(CH_3)_5]_2UCl_2 \cdot Na \cdot nTHF$; D, $[\eta^5-C_5(CH_3)_5]_2ThCH_3][B(C_6F_5)_4]$ E, $[\eta^5-C_5(CH_3)_5]_2ThCH_3][CH_3B(C_6F_5)_3]$; F, $[\eta^5-C_5(CH_3)_5]_2Th(CH_3)_2$; G, $[\eta^5-C_5(CH_3)_5]_2U(CH_3)_2$
[3] MAO (octyl modified) in toluene and IBAO in toluene added via syringe unless otherwise noted. When added in parts, the total amount shown was added in equal portions throughout the reaction.
[4] Initial temperature of the oil bath in which the reactor vessel was immersed.
[5] The value of x is the Poisson distribution coefficient; when the data better fit the Schulz-Flory distribution, the value of $\beta$ is shown.
[6] Conducted in 50% (v/v) $R_3Al$/m-xylene at 100 psig.
[7] Conducted at 150 psig.
[8] Conducted in neat TNOA at 100 psig.
[9] Conducted in 50% (v/v) TEA/1-octene at 100 psig.

TABLE 2 n-Alkane Distribution and Purity, mMol (Area %)[1]

| $C_n$ | Example 1 | Example 11 | Example 13 | Example 20 | Example 25 |
|---|---|---|---|---|---|
| 4 | 23.7 (>99) | 25.4 (>99) | 21.1 (>99) | 28.2 (99) | 19.1 (>99) |
| 6 | 30.3 (98.6)[2] | 28.5 (96.1)[7] | 25.5 (98.4)[3] | 18.5 (94.8)[4] | 22.4 (94.0)[8] |
| 8 | 25.2 (98.6)[2] | 23.0 (nd) | 21.3 (99.9) | 22.6 (96.8)[4] | 23.5 (nd) |
| 10 | 14.6 (>99) | 14.0 (97.6)[5] | 14.2 (99.7) | 13.6 (96.1)[5] | 16.0 (87.7) |
| 12 | 6.72 (>99) | 6.62 (98.4)[3] | 7.50 (99.9) | 6.26 (96.4)[5] | 8.64 (90.7) |
| 14 | 2.88 (>99) | 2.88 (97.7)[2] | 3.75 (>99) | 2.61 (96.1)[6] | 4.29 (88.9) |
| 16 | 1.11 (>99) | 1.13 (98.2)[3] | 1.74 (99) | 0.977 (96.6)[6] | 1.92 (81.5) |
| 18 | 0.408 (nd) | 0.425 (nd) | 0.779 (nd) | 0.354 (nd) | 0.834 (74.0) |
| 20 | 0.135 (nd) | 0.143 (nd) | 0.323 (nd) | 0.117 (nd) | 0.010 (nd) |
| 22 | 0.046 (nd) | 0.051 (nd) | 0.144 (nd) | 0.044 (nd) | 0.007 (nd) |

[1] Abbreviation nd = not determined.
[2] α-Olefin impurity 1.2-1.5 area %.
[3] α-Olefin impurity 1.1 area %.
[4] α-Olefin impurity 3.0-3.5 area %.
[5] α-Olefin impurity 2.0-2.4 area %.
[6] α-Olefin impurity 1.6-1.9 area %.
[7] α-Olefin impurity 3.9 area %.
[8] α-Olefin impurity 6 area %.

What is claimed is:

1. An improved process for the preparation of an aluminum alkyl chain growth product by the chain growth reaction of α-olefin on an aluminum alkyl, the improvement comprising catalyzing the chain growth reaction with a catalyst system which comprises an activated actinide metallocene.

2. The process of claim 1 wherein the α-olefin is ethylene and the aluminum alkyl is represented by the formula $R_MAlH_n$, where m is 2 or 3, n is 0 or 1, $m + n = 3$ and R is $C_2$ to $C_{20}$ alkyl which can be the same or different.

3. The process of claim 2 wherein the actinide is selected from thorium and uranium and the aluminum alkyl is triethylaluminum or tri-n-butylaluminum.

4. The process of claim 1 wherein said catalyst system is selected from:
(A) an uncharged actinide metallocene derivative and a hydrocarbylaluminoxane,
(B) a cationic actinide metallocene complex with a hydrocarbyl or hydride ligand containing an inert, non-coordinating anion, and
(C) a cationic actinide metallocene complex with a hydrocarbyl or hydride ligand containing an inert non-coordinating anion, and a hydrocarbylaluminoxane.

5. The process of claim 4 wherein the α-olefin is ethylene, the actinide metallocene is an uncharged actinide metallocene represented by the formula $Z_t(\eta^5-R'_nH_mC_5)_2MX_{r-s}$ wherein R' is a carbon or carbon and heteroatom containing $C_1$ to $C_{20}$ alkyl, $C_3$ to $C_{12}$ cycloalkyl, $C_7$ to $C_{20}$ aralkyl or a $C_6$ to $C_{14}$ aryl substituent, two or more substituents can form cyclic groups fused to a cyclopentadienyl ring and the R' groups can be different in type and number on each cyclopentadienyl ring, Z is a silane, phosphine, amine or carbon bridging group between two cyclopentadienyl rings, t is 0 or 1, m and n are integers of 0 to 5 and m+n=5 when t is 0 or 4 when t is 1, r is 3 or 4, s is 1 or 2 when r=3 and 1 to 3 when r=4, M is an actinide element and X is halogen, pseudo-halogen, hydride or alkyl and each X can be the same or different, the mole ratio of metallocene to aluminum alkyl is from about $1\times10^{-7}$ to $1\times10^{-1}$, the mole ratio of hydrocarbylaluminoxane to metallocene is from about 5/1 to 50,000/1, the reaction temperature is from about 20° to 150° C. and the ethylene pressure is from about 15 to 1000 psig.

6. The process of claim 5 wherein the actinide element is thorium or uranium.

7. The process of claim 6 wherein the hydrocarbylaluminoxane is a methylaluminoxane.

8. The process of claim 4 wherein the catalyst system is a cationic actinide metallocene complex with a hydrocarbyl or hydride ligand containing an inert, non-coordinating anion.

9. The process of claim 4 wherein the catalyst system is a cationic actinide metallocene complex with a hydrocarbyl or hydride ligand containing an inert non-coordinating anion, and a hydrocarbylaluminoxane.

10. In a process for the preparation of linear alpha-olefins by the chain growth reaction of α-olefin on an aluminum alkyl followed by olefin displacement of linear alpha-olefins from the aluminum alkyl chain growth product, the improvement comprising catalyzing the chain growth reaction with a catalyst system which comprises an activated actinide metallocene.

11. The process of claim 10 wherein the α-olefin is ethylene and the aluminum alkyl is represented by the formula $R_mAlH_n$, where m is 2 or 3, n is 0 or 1, m+n=3 and R is $C_2$ to $C_{20}$ alkyl which can be the same or different.

12. The process of claim 11 wherein the actinide is selected from thorium and uranium and the aluminum alkyl is triethylaluminum or tri-n-butylaluminum.

13. The process of claim 10 wherein said catalyst system is selected from:
(A) an uncharged actinide metallocene derivative and a hydrocarbylaluminoxane,
(B) a cationic actinide metallocene complex with a hydrocarbyl or hydride ligand containing an inert, non-coordinating anion, and
(C) a cationic actinide metallocene complex with a hydrocarbyl or hydride ligand containing an inert non-coordinating anion, and a hydrocarbylaluminoxane.

14. The process of claim 13 wherein the α-olefin is ethylene, the actinide metallocene is an uncharged actinide metallocene represented by the formula $Z_t(\eta^5-R'_nH_mC_5)_2MX_{r-s}$ wherein R' is a carbon or carbon and heteroatom containing $C_1$ to $C_{20}$ alkyl, $C_3$ to $C_{12}$ cycloalkyl, $C_7$ to $C_{20}$ aralkyl or a $C_6$ to $C_{14}$ aryl substituent, two or more substituents can form cyclic groups fused to a cyclopentadienyl ring and the R' groups can be different in type and number on each cyclopentadienyl ring, Z is a silane, phosphine, amine or carbon bridging group between two cyclopentadienyl rings, t is 0 or 1, m and n are integers of 0 to 5 and m+n=5 when t is 0 or 4 when t is 1, r is 3 or 4, s is 1 or 2 when r=3 and 1 to 3 when r=4, M is an actinide element and X is halogen, pseudo-halogen, hydride or alkyl and each X can be the same or different, the mole ratio of metallocene to aluminum alkyl is from about $1\times10^{-7}$ to $\times10^{-1}$, the mole ratio of hydrocarbylaluminoxane to metallocene is from about 5/1 to 50,000/1, the reaction temperature is from about 20° to 150° C. and the ethylene pressure is from about 15 to 1000 psig.

15. The process of claim 14 wherein the actinide element is thorium or uranium.

16. The process of claim 15 wherein the hydrocarbylaluminoxane is a methylaluminoxane.

17. The process of claim 13 wherein the catalyst system is a cationic actinide metallocene complex with a hydrocarbyl or hydride ligand containing an inert, non-coordinating anion.

18. The process of claim 13 wherein the catalyst system is a cationic actinide metallocene complex with a hydrocarbyl or hydride ligand containing an inert non-coordinating anion, and a hydrocarbylaluminoxane.

19. In a process for the preparation of linear primary alcohols by the chain growth reaction of α-olefin on an aluminum alkyl followed by oxidation of the aluminum alkyl chain growth product to form alkoxides and acid hydrolysis of the alkoxides to produce linear primary alcohols, the improvement comprising catalyzing the chain growth reaction with a catalyst system which comprises an activated actinide metallocene.

20. The process of claim 19 wherein the α-olefin is ethylene and the aluminum alkyl is represented by the formula $R_mAlH_n$, where m is 2 or 3, n is 0 or 1, m+n=3 and R is $C_1$ to $C_{20}$ alkyl which can be the same or different.

21. The process of claim 20 wherein the actinide is selected from thorium and uranium and the aluminum alkyl is triethylaluminum or tri-n-butylaluminum.

22. The process of claim 19 wherein said catalyst system is selected from:
(A) an uncharged actinide metallocene derivative and a hydrocarbylaluminoxane,
(B) a cationic actinide metallocene complex with a hydrocarbyl or hydride ligand containing an inert, non-coordinating anion, and
(C) a cationic actinide metallocene complex with a hydrocarbyl or hydride ligand containing an inert non-coordinating anion, and a hydrocarbylaluminoxane.

23. The process of claim 22 wherein the α-olefin is ethylene, the actinide metallocene is an uncharged actinide metallocene represented by the formula $Z_t(\eta^5-R'_nH_mC_5)_xMX_{r-s}$ wherein R' is a carbon or carbon and heteroatom containing $C_1$ to $C_{20}$ alkyl, $C_3$ to $C_{12}$ cycloalkyl, $C_7$ to $C_{20}$ aralkyl or a $C_6$ to $C_{14}$ aryl substituent, two or more substituents can form cyclic groups fused to a cyclopentadienyl ring and the R' groups can be different in type and number on each cyclopentadienyl ring, Z is a silane, phosphine, amine or carbon bridging group between two cyclopentadienyl rings, t is 0 or 1, m and n are integers of 0 to 5 and m+n=5 when t is 0 or 4 when t is 1, r is 3 or 4, s is 1 or 2 when r=3 and 1 to 3 when r=4, M is an actinide element and X is halogen, pseudo-halogen, hydride or alkyl and each X can be the same or different, the mole ratio of metallocene to aluminum alkyl is from about $1\times10^{-7}$ to $1\times10^{-1}$, the mole ratio of hydrocarbylaluminoxane to metallocene is from about 5/1 to 50,000/1, the reaction temperature is from about 20° to 150° C. and the ethylene pressure is from about 15 to 1000 psig.

24. The process of claim 23 wherein the actinide element is thorium or uranium.

25. The process of claim 24 wherein the hydrocarbylaluminoxane is a methylaluminoxane.

26. The process of claim 22 wherein the catalyst system is a cationic actinide metallocene complex with a hydrocarbyl ligand or hydride containing an inert, non-coordinating anion.

27. The process of claim 22 wherein the catalyst system is a cationic actinide metallocene complex with a hydrocarbyl ligand or hydride containing an inert non-coordinating anion, and a hydrocarbylaluminoxane.

28. The process of claim 2 which includes a solvent diluent comprising one or more higher alpha-olefins.

29. The process of claim 11 which includes a solvent diluent in said chain growth reaction, said diluent comprising one or more higher alpha-olefins.

30. The process of claim 20 which includes a solvent diluent in said chain growth reaction, said diluent comprising one or more higher alpha-olefins.

* * * * *

UNITED STATES PATENT AND TRADEMARK OFFICE
CERTIFICATE OF CORRECTION

PATENT NO. : 5,276,220
DATED : January 4, 1994
INVENTOR(S) : Edward G. Samsel, et al.

It is certified that error appears in the above-identified patent and that said Letters Patent is hereby corrected as shown below:

Claim 5, line 18 reads "...-$R'_n H_m C_5)_2 MX_{r-s}$...", but should read
-- ...-$R'_n H_m C_5)_s MX_{r-s}$... --

Claim 14, line 25 reads "...to X $10^{-1}$,...", but should read
-- ...to 1 X $10^{-1}$,... --.

Claim 23, line 4 reads "...-$R'_n H_m C_5)_x MX_{r-s}$...", but should read
-- ...-$R'_n H_m C_5)_s MX_{r-s}$... --.

Signed and Sealed this

Twelfth Day of July, 1994

BRUCE LEHMAN

Attest:

Attesting Officer         Commissioner of Patents and Trademarks